United States Patent [19]
Bonne

[11] Patent Number: 5,311,447
[45] Date of Patent: May 10, 1994

[54] ON-LINE COMBUSTIONLESS MEASUREMENT OF GASEOUS FUELS FED TO GAS CONSUMPTION DEVICES

[76] Inventor: Ulrich Bonne, 4936 Shady Oak Rd., Hopkins, Minn. 55343

[21] Appl. No.: 126,097

[22] Filed: Sep. 23, 1993

Related U.S. Application Data

[63] Continuation of Ser. No. 781,598, Oct. 23, 1991, abandoned.

[51] Int. Cl.$^5$ ................ G01N 11/00; G01N 25/18; G06F 15/20
[52] U.S. Cl. .................. 364/509; 374/44; 73/25.03; 364/557
[58] Field of Search .............. 364/509, 557, 558; 73/204.16, 204.17, 25.03; 374/44

[56] References Cited

U.S. PATENT DOCUMENTS

| | | | |
|---|---|---|---|
| 4,265,125 | 5/1981 | Mahany | 374/117 |
| 4,337,654 | 7/1982 | Austin et al. | 374/37 |
| 4,345,463 | 8/1982 | Wilson et al. | 374/36 |
| 4,384,472 | 5/1983 | Tournier | 73/30.01 |
| 4,384,792 | 5/1983 | Sommers et al. | 29/890.06 |
| 4,386,858 | 6/1983 | Kude et al. | 374/37 |
| 4,444,337 | 4/1984 | Kude et al. | 222/139 |
| 4,613,482 | 9/1986 | Cheney | 422/51 |
| 4,630,938 | 12/1986 | Piorkowska-Palczewska et al. | 374/44 |
| 4,674,322 | 6/1987 | Stangeland | 73/32 A |
| 4,885,938 | 12/1989 | Higashi | 73/204.18 |
| 4,944,035 | 7/1990 | Aagardl et al. | 364/556 |
| 4,956,793 | 9/1990 | Bonne et al. | 364/558 |

OTHER PUBLICATIONS

"Low-Cost Gas BTU Meter Using Physical Property Measurements", Phase III Final Report, Gas Research Institute, Dec. 1984.
"Microstructures Sensors for Flow, Differential Pressure and Energy Measurement", Honeywell, Inc., Physical Sciences and Technology Center, presented at IGT Symposium on Natural Gas Energy Measurement, Chicago, Ill., Apr., 1986.
"Energy Flow Meter Development", Phase I–Gas Sampling Method, Phase II–Prototype Energy Flow Meter, Gas Research Institute, Annual Report, Dec., 1983.

Primary Examiner—Thomas G. Black
Assistant Examiner—Michael Zanelli
Attorney, Agent, or Firm—Heslin & Rothenberg

[57] ABSTRACT

A combustionless measurement method and apparatus are described for ascertaining the quality and/or quantity of gaseous fuels fed to gas consumption devices, and particularly natural gas consumption devices. The technique utilizes a novel empirical algorithm for correlating easily measured gas parameters to any one of the: heating value of the fuel gas; density of the fuel gas; and percent concentration of inert gases within the fuel gas. Sensed fuel gas parameters can include any combination of viscosity, thermal conductivity, specific heat, and optical absorption, etc., at more than one temperature if needed for accuracy. Specific structures are set forth for implementing the technique.

19 Claims, 8 Drawing Sheets

THERMAL DIFFUSIVITY SENSOR
OR SPECIFIC HEAT SENSOR

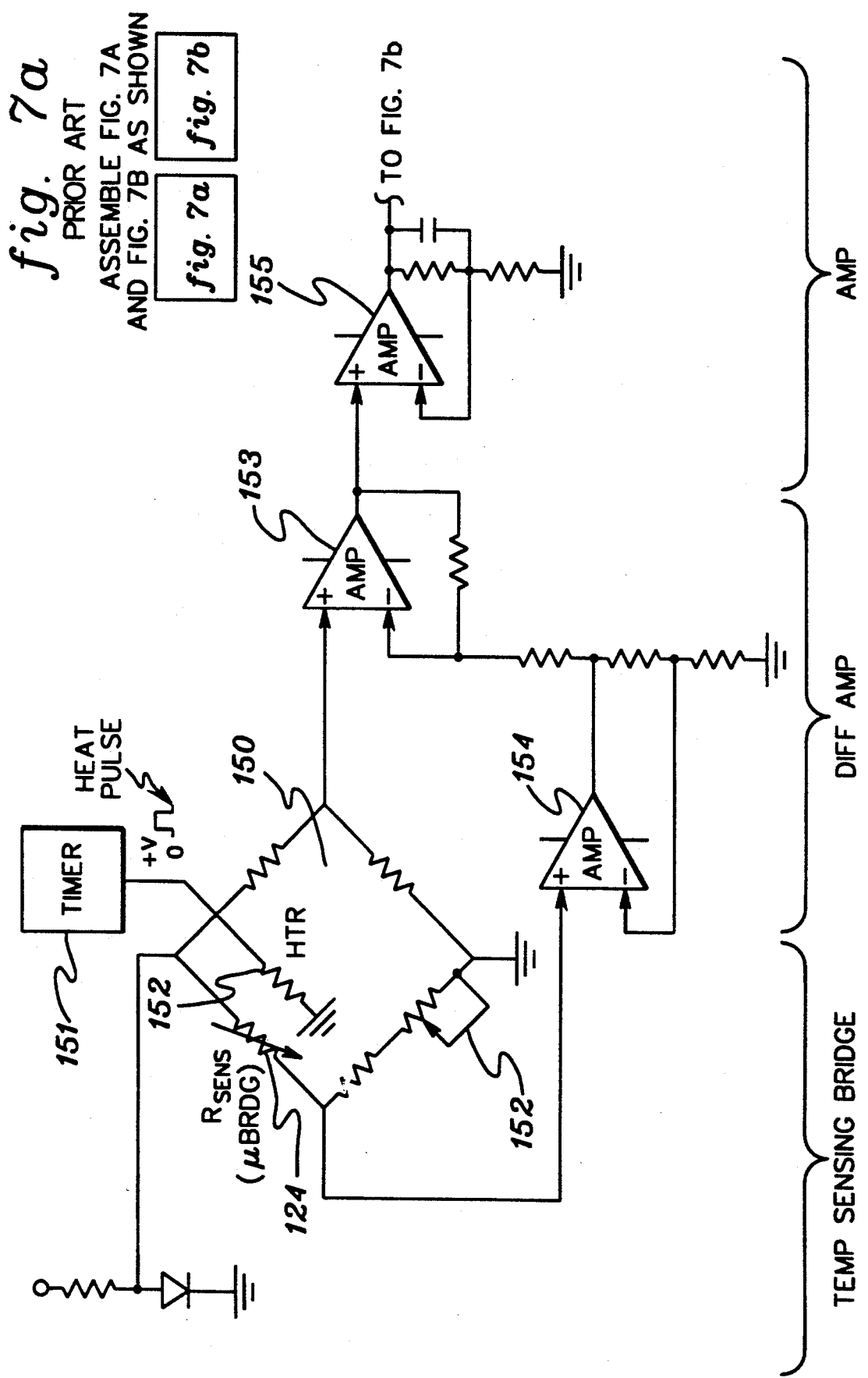

ON-LINE COMBUSTIONLESS MEASUREMENT OF GASEOUS FUELS FED TO GAS CONSUMPTION DEVICES

This application is a continuation of application Ser. No. 07/781,598, filed Oct. 23, 1991 now abandoned.

BACKGROUND OF THE INVENTION

1. Technical Field

The present invention relates to methods for the combustionless measurement of the quality of gaseous fuels fed to gas consumption devices, and particularly natural gas consumption devices, as well as apparatus for the carrying out of the different variations of the process.

2. Description of the Prior Art

The heating value of a substance is of significant interest because it forms one basis for determining the commercial value of that substance as a fuel. Methods for measuring the quality of gaseous fuels to ascertain the amount of heat available therefrom are already being used in practice for numerous purposes. Recently, interest in and need for such measurements have increased considerably for various reasons. In industrial heating processes, it is frequently necessary to feed a well defined amount of heat per unit of time to a furnace in order to obtain optimum results. In other cases it is desirable to optimize the consumption of fuel, i.e., to feed only the amount of heat actually required even if supplying a larger amount of heat does not adversely affect the process or product. For accounting purposes, billing on the basis of the amount of heat supplied has also been preferred to billing on a volume basis.

An extensive need has arisen, therefore, for measurements of the quality of a gaseous fuel. Unfortunately, gas quality measurement is complicated by the fact that combustion gases, and particularly natural gases, are typically distributed together notwithstanding separate origin, composition and properties that differ to a greater or lesser extent from each other. Since processes and apparatus have proven themselves for use with such distributed gases of different composition, the on-line measurement of the quality of the gas or the quantity of heat available therefrom has gained increasing importance for the industrial use of gas and for accounting purposes.

Known methods for evaluating gas quality are in most cases not readily adaptable to these uses due to technical reasons or because of cost considerations. For example, one conventional method for measuring heating value known in the art comprises combustion calorimetry. This process involves the burning of a partial stream of the combustible gas with an open flame or with a catalyst and measuring the heat produced. The necessity of burning a measured partial stream of the gas in order to determine its heating value, as known from experience, requires frequent maintenance of the apparatus, since a flame can change due to deposits of combustion residues or because a combustion catalyst gradually declines in effectiveness. The required accuracy of measurements which serve, for example, for billing purposes can only be obtained if these apparatus are operated under well-defined, controlled conditions, preferably in an air-conditioned chamber, which is obviously expensive.

Other known non-combustion methods for continuously analyzing a stream of gas include gas chromatography and mass spectrometry. Gas chromatography and mass spectrometry are techniques for separating and identifying each constituent of the gas and measuring the relative concentration thereof. Knowing the heating value of each constituent of a mixture, the total heating value may then be computed. Unfortunately, these methods require a large expenditure of measurement and control devices to implement.

The same techniques are also currently used to determine other parameters representative of the quality of a distributed fuel gas, such as density and percent concentration of inert gases therein. A principle use for gas density determination is in the operation of an orifice flow meter, while percent concentration of inert gases, for example, nitrogen, $N_2$, carbon dioxide, $CO_2$, and oxygen, $O_2$, is used to determine gas pumping/transportation cost or for subsequent regulation of a combustion process.

To summarize, most, if not all, presently known techniques for determining the quality of a fuel gas, such as heating value, density or percent concentration of inert gases, have one or more drawbacks associated therewith, including: requiring trained personnel to operate, producing time delayed results, lacking repeatability, destroying the sample, being cumbersome or expensive to implement and lacking sufficient accuracy due to an inability to completely distinguish constituents. Therefore, there exists a genuine need in the art for a novel approach to the measurement of the quality of a fuel gas which is accurate, reliable and inexpensive in implementation.

SUMMARY OF THE INVENTION

The primary object of the present invention is to provide a process and apparatus capable of determining the quality of a combustible gas without the combustion of the gas and in a simpler manner than with previously known combustionless methods.

Another object of the present invention is to provide such a process and apparatus which are more readily adaptable to field installation than conventional techniques for effecting such measurements.

Yet another object of the present invention is to provide such a process and apparatus which are capable of determining the heating value, density or percent concentration of gas inerts of the fuel gas.

A further object of the present invention is to provide such a process and apparatus which are capable of determining one or more of the heating value, density and percent concentration of inerts within the fuel gas from the same readily measured gas parameters.

The foregoing and other objects are accomplished in accordance with the present invention in part through the discovery of an empirical formula correlating certain readily measurable gas parameters with the desired measurement, i.e., heat content, density or percent concentration of gas inerts. In their broadest aspect, the process and apparatus recited herein utilize a formula of the form:

$$\mu = a_o + b_1 n_{t1}^{n1} + b_2 n_{t2}^{n2} + \ldots + c^1 k_{t1}^{m1} + c_2 k_{t2}^{m2} + \ldots + d_1 c_{pt1}^{p1} + d_2 c_{pt2}^{p2} + \ldots + e_1 A_{t1}^{u1} + e_2 A_{t2}^{u2} + \ldots \quad (1)$$

where:
$a_o, b_1, b_2, c_1, c_2, d_1, d_2, e_1, e_2$ = constants;
$n1, n2, m1, m2, p1, p2, u1, u2$ = exponents;
$n_{ti}$ = viscosity at various temperatures, ti;
$k_{ti}$ = thermal conductivities at various temperatures, ti;

$c_{pti}$ = specific heat at various temperatures, ti; and
$A_{ti}$ = optical absorption at various temperatures, ti.

Those skilled in the art will appreciate that additional, readily measured gas parameters, such as speed of sound, may also be incorporated into the above formula, provided the overall novel form of the equation is maintained. Also, one or more measured terms, for example, viscosity, specific heat and/or optical absorption, may be omitted from the formula if unnecessary to attaining a desired accuracy level. At least two different terms are believed necessary, however.

By way of example, in one specific embodiment applicant's empirical formula is expressed as:

$$\mu = a_0 + b_1 f(n)^{o1} + c_1 f_1(k_{t1}, k_{t2})^{m1} + c_2 f_2(k_{t1}, k_{t2})^{m2} \quad (2)$$

where:

$\mu$ = heat content, density or percent gas inerts calculation;
$a_0, b_1, c_1$ & $c_2$ = constants;
o1, m1 & m2 = exponents;
n = viscosity;
$k_{t1}$ = thermal conductivity at a first temperature; and
$k_{t2}$ = thermal conductivity at a second temperature.

Prior to ascertaining a desired value (i.e., heat content, density or percent concentration of gas inerts), applicant's method requires the steps of: conducting at least a partial stream of the fuel gas through a sensor chamber having a plurality of sensors in contact with a fuel gas; generating a first electrical signal at one of the plurality of sensors, the first electrical signal being representative of a first fuel gas quality, the first fuel gas quality comprising one of thermal conductivity, specific heat, viscosity and optical absorption; conducting the first electrical signal to a computing means; generating a second electrical signal at one of the plurality of sensors, the second electrical signal being representative of a second fuel gas quality, the second fuel gas quality comprising one of thermal conductivity, specific heat, viscosity and optical absorption, the second fuel gas quality comprising a different one of the fuel gas qualities than the first gas quality; conducting the second electrical signal to the computer means; and finally, using said computing means to derive a signal for at least one of measurement utilizing the first and second electrical signals as a measure for at least one of the heat content, density and percent gas inerts of the fuel gas according to formula:

$$\mu = a_0 + b_1 x^{m1} + c_1 y^{p1}$$

where:

$\mu$ = said at least one of said fuel gas heat content, density and percent concentration of gas inerts,
+ = represents one of addition, subtraction, multiplication and division,
$a_0, b_1, c_1,$ = constants,
m1, p1, = exponents,
x = signal representative of the first fuel gas quality, and
y = signal representative of the second fuel gas quality.
Specific values for the constants and exponents, which have been defined by applying linear progression analysis to experimental test results, are provided.

In another aspect, the present invention comprises a corresponding apparatus for the combustionless measurement of fuel gas. The apparatus includes a sensor chamber having a plurality of sensors therein and conducting means for moving at least a partial stream of the fuel gas through the sensor chamber such that the gas is in contact with the plurality of sensors. First generating means is provided for producing a first electrical signal at one of the plurality of sensors. The first electrical signal is representative of a first fuel gas quality, which comprises one of thermal conductivity, specific heat, viscosity and optical absorption of the fuel gas. Transferring means conducts the first electrical signal to a computer for processing. A second generating means is also included for generating a second electrical signal at one of the plurality of sensors. The second electrical signal is representative of a second fuel gas quality which is different from the first fuel gas quality. The second fuel gas quality comprises one of thermal conductivity, specific heat, viscosity and optical absorption of the fuel. Again, transferring means conducts the second electrical signal to the computer for processing. The computer is then used to periodically derive a signal for at least one of measurement and regulation using the first and second generated electrical signals as a measure for at least one of the heat content, density and percent gas inerts of the fuel gas according to the formula:

$$\mu = a_0 + b_1 x^{m1} + c_1 y^{p1}$$

where:

$\mu$ = said one of said fuel gas heat content, density and percent concentration of gas inerts,
+ = one of addition, subtraction, multiplication and division,
$a_0, b_1, c_1,$ = constants,
m1, p1, = exponents,
x = signal representative of the first fuel gas quality, and
y = signal representative of the second fuel gas quality.

In a preferred form, the plurality of sensors comprise microsensors which are arranged within the chambers such that substantially zero gas flow is encountered thereby. Additional embodiments of the process and apparatus of the present invention are described below.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings in which:

FIGS. 7A and 7B are a more detailed circuit schematic with reference to FIG. 4(c)

DETAILED DESCRIPTION OF THE INVENTION

As briefly set forth above, central to the manner of technical action which forms the subject matter of this invention, as defined in the attached process and apparatus claims, is the surprising discovery that heat content, density and percent concentration of gas inerts may each be readily and accurately determined from an empirical expression, for example, of the form:

$$\mu = a_o + b_1 f(n)^{o1} + c_1 f_1(k_{t1}, k_{t2})^{m1} + c_2 f_2(k_{t1}, k_{t2})^{m2} \quad (2)$$

where:

$\mu$ = heat content, density or percent gas inerts calculation;

$a_o, b_1, c_1$ & $c_2$ = constants;

o1, m1 & m2 = exponents;

n = gas viscosity;

$k_{t1}$ = gas thermal conductivity at a first temperature, t1; and $k_{t2}$ = gas thermal conductivity at a second temperature, t2.

(Units for the various measured parameters and calculations are set forth in Table II.) Applicant has also discovered that several other readily measured parameters characteristic of the fuel gas, such as specific heat, $c_p$, and optical absorption, A, may be determined and used to supplement, or substitute for, the viscosity, n, and thermal conductivity, k, variables of equation (2) (e.g., see equation (1) above and equation (8) below). Notwithstanding the utilization of different gas parameter combinations, however, the overall form of equations (1), (2), (8), etc., is maintained. (As set forth, equation (2) in part expresses gas thermal conductivity as a function of two readings $k_{t1}$ and $k_{t2}$ (e.g., see equations (3)-(7) below). One skilled in the mathematics art could separate these terms if desired to attain a formula more clearly of the form of equation (1). All the gas parameters discussed herein are readily measurable using existing technology, but preferred implementing processes and apparatus are described, and claimed, below.

Specific algorithm examples are provided herein for determining the quality of natural gases. However, applicant believes that the empirical formula is equally applicable to other types of fuel gases and that one of ordinary skill can derive the necessary specific equations therefor from the information provided herein.

Figure 1:
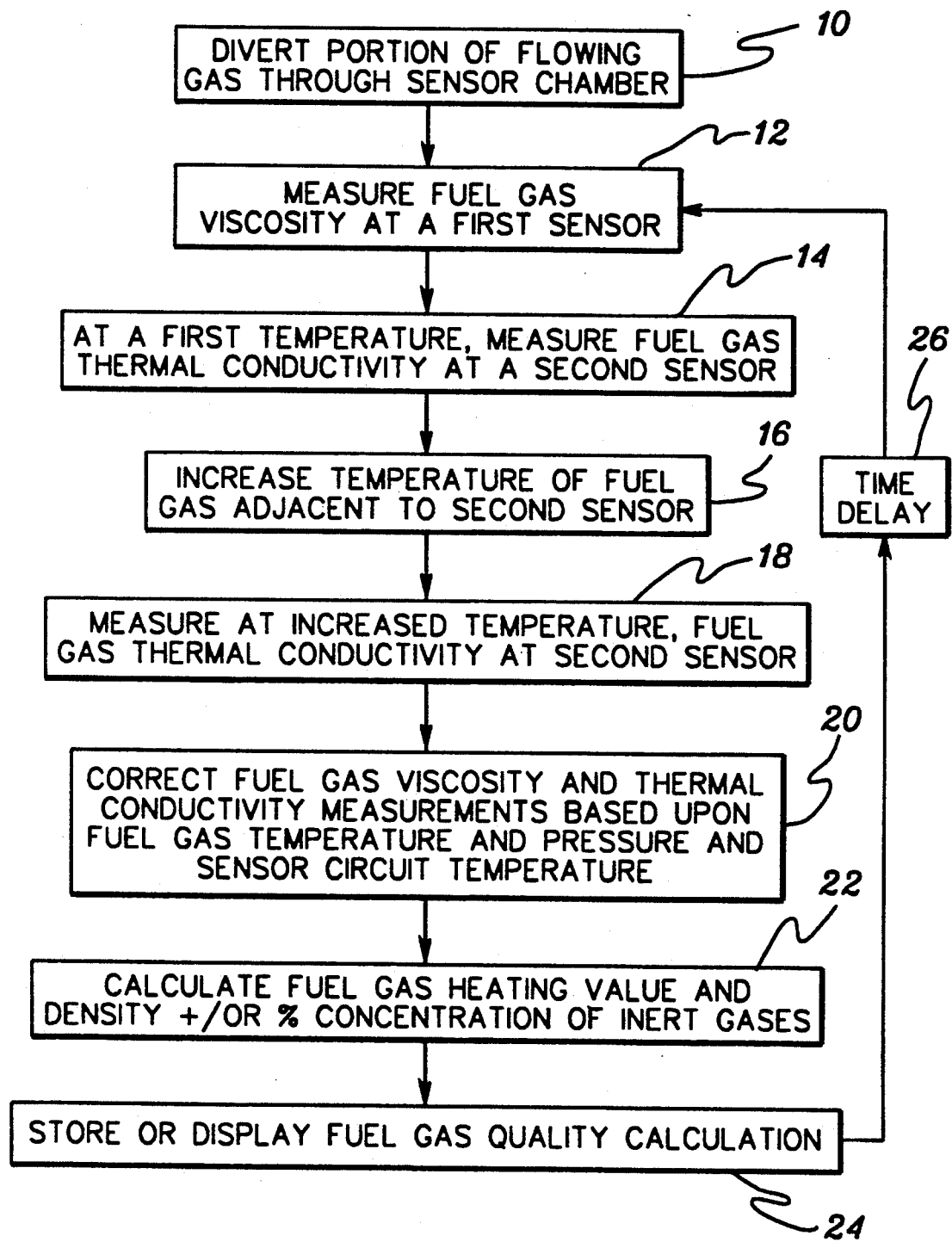
FIG. 1 is an operational overview of one process embodiment of the present invention.

FIG. 1 depicts one operational overview of a method of the present invention implemented using the algorithm of equation (2). Initially, a portion of the fuel gas must be diverted through a sensor chamber (discussed below), 10 "Divert Portion Of Flowing Fuel Gas Through Sensor Chamber." First and second measurements 12 "Measure Fuel Gas Viscosity At A First Sensor" and 14 "At A First Temp., Measure Fuel Gas Thermal Conductivity At A Second Sensor," respectively, are taken. Thereafter the temperature of the fuel gas at the second sensor is increased, 16 "Increase Temp. Of Fuel Gas Adjacent Second Sensor," and the fuel gas thermal conductivity at the increased temperature is determined, 18 "Measure At Increased Temp. Fuel Gas Conductivity At Second Sensor." In the preferred embodiment, an increase in fuel gas temperature adjacent the second sensor is readily attained by increasing the current though a microbridge structure (described below) used to obtain the thermal conductivity measurements. The two temperatures at which gas thermal conductivity is measured should be selected to optimize the signal to noise ratio of the resultant microbridge output. If too low a temperature is initially selected as t1, the difference signal is not strong enough, and if too high a second temperature is chosen for t2, the operational lifetime of the sensor will be short. Approximately 70° C. and 120° C. are believed to be examples of acceptable first temperature, t1, and second temperature, t2, values for ascertaining gas thermal conductivity with the arrangement described herein.

Next, the method requires correction of measured viscosity and thermal conductivity values to account for influences of gas temperature, gas pressure and circuit temperature changes, 20 "Correct Fuel Gas Viscosity and Thermal Conductivity Measurements Based Upon Fuel Gas Temp. and Pressure, and Sensor Circuit Temp." Viscosity and thermal conductivity values can also be converted to standardized readings using the measured absolute pressure and temperature of the fuel gas. Equation (2) is then used to determine the desired heating value, density or percent concentration of gas inerts value for the fuel gas, 22 "Calculate Fuel Gas Heating Value, Density and/or Percent Concentration of Inert Gases." This value is then either stored or displayed, 24 "Store or Display Fuel Gas Quality Calculation," and thereafter flow returns to step 12, i.e., subsequent a time delay, 26 "Time Delay." Time delay 26 must be sufficient for the thermal conductivity sensor to return to first temperature level t1, i.e., the temperature of the sensor chamber. With a microbridge sensor configuration as described below, this only requires a few milliseconds.

By way of more specific example, formula (2) is first used in the process and apparatus of the present invention to combustionlessly determine the heating value or heat content of a fuel gas, such as a natural or synthetic fuel.

With the use of any commercially available linear progression analysis program, one specific equation for deriving the heat content of a natural gas, which takes the form of equation (2), comprises:

$$H_c = 3643.53 + 1050.71(102/n)^3 - 7.60221 k_{t2} - 2294.2(k_{t2}/k_{t1}) \quad (3)$$

where:

$H_c$ = gas heat content;

n = viscosity;

$k_{t1}$ = gas thermal conductivity at a first temperature, t1; and $k_{t2}$ = gas thermal conductivity at a second temperature, t2.

Although preferred techniques for measuring viscosity and thermal conductivity are described below, both parameters can be readily determined by one of ordinary skill in the art using presently available technology. For example, viscosity is measurable by determining the pressure drop across a capillary through which a known volume of gas is pumped with a positive displacement pump and thermal conductivity can be determined using a conventional wheatstone bridge circuit. From extensive testing, applicant has determined that utilization of equation (3) to determine heat content of a natural gas results in a maximum error of 0.06696 MJ/m³, with a standard error of 0.01831 MJ/m³. This result is considered well within acceptable error limits imposed by the industry.

Once obtained, derived heat content values are indicated or transmitted to recording instruments or given off as control pulses depending upon the measurement and/or regulation information required for a particular application. The process and arrangement are also suitable for installation in measurement stations of high-pressure, long distance gas transmission (pipe) lines in which the (heat) quantity of flow is continuously recorded.

An important benefit flowing from utilization of a formula of the type of equations (1) and (2) is the synergistic benefits obtained therefrom when incorporated into a process and arrangement as claimed herein. Namely, any one of heat content, density and percent concentration of gas inerts of the fuel gas may be readily computed using the same basic measurements, e.g., viscosity and thermal conductivity, and the same basic algorithm type, e.g. equation (1), (2), or (8). This is because each of these values comprises a measure of the "quality" of the fuel gas.

Fuel gas density determination is important to computing the orifice coefficient of the gas, which is necessary for operation of a typical orifice flow meter, along with determining gas compressibility factors and densitometer calculations. By using formula (2), the present invention provides an inexpensive and accurate means for ascertaining density of a natural gas. Applying linear progression analysis to equation (2) and independently derived density readings, one specific formula for determining the density of natural gas is obtained:

$$\rho = 4.3077 + 0.22937(102/n)^3 - 0.012094 k_{t1} - 2.2881(k_{t2}/k_{t1}) \quad (4)$$

where:
$\rho$ = gas density;
n = gas viscosity;
$k_{t1}$ = gas thermal conductivity at a first temperature, t1; and
$k_{t2}$ = gas thermal conductivity at a second temperature, t2.

As noted, quantifying of percent concentration of inert gas has traditionally been accomplished with sophisticated, costly and labor intensive means, such as gas chromatography equipment. Accurate determination of inert gases like nitrogen, $N_2$, carbon dioxide, $CO_2$, and oxygen, $O_2$ in fuel gas, and particularly natural gas, is important because these gases reduce the heating value of the fuel gas, cause the pumping/transportation cost per unit of gas energy to be increased, and reduce the supplier's revenue per delivered unit volume of gas, etc. Through extensive experimentation and testing, equations (5)–(7) below have been identified as being preferred specific forms of formula (2) for various combinations of inert gases within natural gas. Again, the constants and exponents were determined by applying linear progression analysis to independently measured results.

$$X_{N2+O2+CO2} = 288.69 - 23.818/n^3 - 0.59575 k_{t1} - 173.65(k_{t2}/k_{t1}) \quad (5)$$

$$X_{N2+O2} = 464.65 + 9.8185/n^3 - 0.42180 k_{t1} - 356.18(k_{t2}/k_{t1}) \quad (6)$$

$$X_{CO2} = -175.96 - 33.636/n^3 - 0.17395 k_{t1} + 182.52(k_{t2}/k_{t1}) \quad (7)$$

where:
$X_{N2+O2+CO2}$ = % concentration of $N_2$, $O_2$ and $CO_2$ in fuel gas,
$X_{N2+O2}$ = % concentration of $N_2$ and $O_2$ in fuel gas,
$X_{CO2}$ = % concentration of $CO_2$ in fuel gas,
n = fuel gas viscosity,
$k_{t1}$ = gas thermal conductivity at a first temperature, t1 and
$k_{t2}$ = gas thermal conductivity at a second temperature, t2.

As noted briefly above, specific heat and optical absorption comprise two additional readily measurable fuel gas characteristics which may be added to formula (2), e.g., to improve accuracy of the resultant computations, or to substitute for one or the other of the viscosity and thermal conductivity variables. A generalized expression of the discovered algorithm is equation (1) above. Table I lists several specific algorithms for calculating heating value of natural gas which have been derived from formula (1) and their measured accuracy levels. The formulas of Table I are considered merely illustrative of various parameter combinations possible pursuant to the invention described herein. From the present description, other specific formulas for determining heating value, density and/or percent concentration inerts can be readily derived by a person skilled in the art. The appended process and arrangement claims are operable with any such formula of a form derived from equation (1).

In addition to the above, applicant has discovered that another particularly preferred expression for determining heat content of a natural gas comprises:

$$H_c = -1287.7 + 808,700 C_p{}^{0.73846} - 1,048,800 k^{-1.742} - 0.00090189(Mn)^{1.7514} \quad (8)$$

where:
$c_p$ = specific heat of the fuel gas;
k = gas thermal conductivity;
Mn = (molecular weight of the gas)·(viscosity of the gas).

The term molecular weight times viscosity, Mn, or its alternate expression density ($\rho$) times viscosity, $\rho n$, is capable of being determined using a combination of available technologies. However, this quantity is preferably ascertained with the novel process and apparatus described in a copending U.S. patent application entitled "Multiple Gas Property Sensor", Ser. No. 07/781,770, now U.S. Pat. No. 5,235,844 (see below for further discussion).

TABLE I

| # | Equation | Max. Error $MJ/m^3$ | Std. Error $MJ/m^3$ |
|---|---|---|---|
| 1) | $H_c = 3643.53 + 1050.71(102/n)^3 - 7.60221 k_{t1} - 12294.2 k_{t2}/k_{t1}$ | .067 | .018 |
| 2) | $H_c = 99333756 k_{t1}{}^{-2.7401} \times k_{t2}{}^{3.4684} \times c_p{}^{1.66326}$ | .084 | .024 |
| 3) | $H_c = 1794792 A^{.46555} \times n^{-1.53904}$ | .037 | .0086 |
| 4) | $H_c = 388886800 k_{t1}{}^{-.057705} \times$ | .079 | .027 |

TABLE I-continued

| # | Equation | Max. Error MJ/m³ | Std. Error MJ/m³ |
|---|---|---|---|
| | $c_p^{.71355} \times n^{-1.48146}$ | | 5 | where:
× = multiplication
$H_c$ = heat content of the fuel gas
$k_{t1}$ = thermal conductivity of fuel gas at temperature t1
$k_{t2}$ = thermal conductivity of fuel gas at temperature t2
$c_p$ = specific heat of fuel gas
A = optical absorption of fuel gas
n = viscosity of fuel gas The implementing apparatus of the invention will now be described in greater detail with reference to accompanying FIGS. 2-8.

Figure 2:
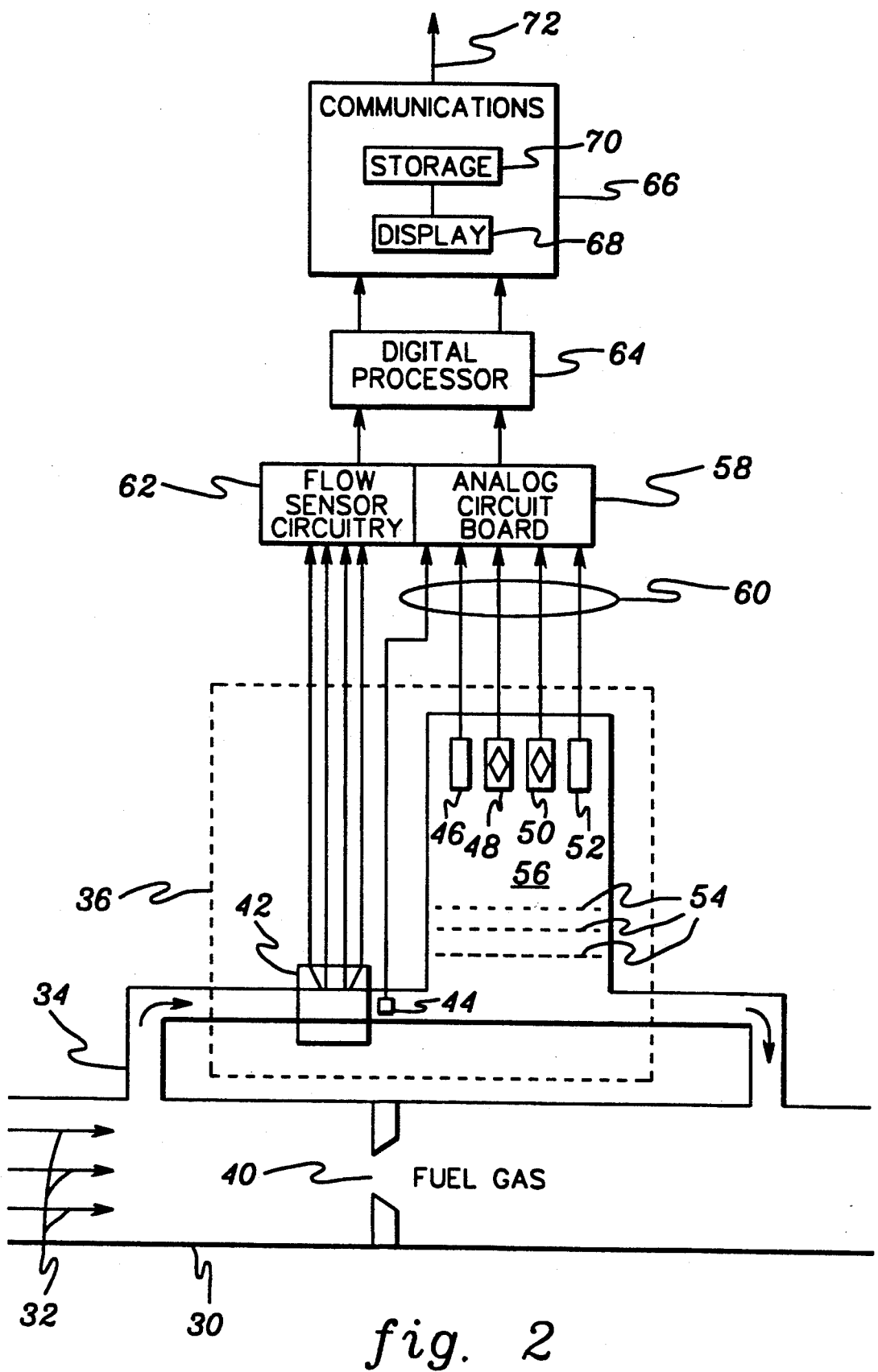
FIG. 2 is a schematic illustration of one embodiment of the apparatus of the present invention.

Referring first to FIG. 2, a structural implementation of one embodiment of the invention is shown. A fuel gas, such as natural gas, flows in main gas line 30 in the direction of arrows 32. A secondary gas inlet pipe 34 is provided for diverting a portion of the gas flow to a sensor chamber 36. The diverted gas is returned from chamber 36 to main line 30 via a gas outlet pipe 38, which connects to line 30 downstream from sensor chamber 36. A constriction 40 within main line 30 creates a pressure differential which forces a portion of the gas flow through sensor chamber 36. Radial dimensions for line 30 and inlet and outlet pipes 34 and 38 may vary, but as an example, main line 30 is typically one to three inches in diameter, while pipes 34 & 38 are approximately one-quarter inch in diameter.

As shown, chamber 36 is located above main line 30, which minimizes condensation effects within the chamber. Sensor chamber 36 preferably comprises a metallic block into which inlet pipe 34 passes and from which outlet pipe 38 extends. Within the block is an airflow sensor 42, a first pressure sensor 44 and a plurality of sensors 46, 48, 50 and 52, which, in the embodiment illustrated, are separated from gas flow by several flow blocking screens 54 such that substantially zero flow effects are encountered within area 56 of chamber 36 adjacent said sensors. As discussed below, sensors 46, 48, 50 and 52 preferably comprise microsensors because of their relative inexpensive cost and high accuracy. However, since these sensors are flow sensitive, screens 54 are needed to create area 56 of minimal flow. Screens 54, e.g., manufactured of a fine wire mesh, are designed to prevent microscopic gas flow to area 56. A plurality of screens is used to ensure that fuel gas essentially only diffuses to area 56. A certain amount of turbulence exists within chamber 36 below screens 54. Sensors 44, 46, 48, 50 & 52 are electrically connected to an analog circuit board 58 via lead lines 60, which are electrically insulated from one another to prevent shorting. Leads 60 serve to connect the inside of sensor chamber 36 to the outside of the chamber. Preferably, insulation (not shown) surrounds chamber 36 to facilitate maintenance of a constant temperature therein.

In one embodiment, sensor 46 comprises a pressure sensor; sensor 48, a gas temperature sensor; sensor 50, a thermal conductivity sensor; and sensor 52, a viscosity sensor. In general, sensors 50 & 52 provide the information needed for calculation of heating value, density or percent gas inerts, e.g., using formula (2), while sensors 44, 46 & 48 allow for correction of sensed thermal conductivity and viscosity values for influences of pressure and temperature in a well known manner. In an alternate embodiment described below, only one sensor, e.g., sensor 48, is required to obtain the parameters necessary (i.e., thermal conductivity and specific heat) to determine heating value, density and/or percent gas inerts.

Flow sensor circuitry 62 is provided to translate flow sensed at 42 into digitally readable signals. Sensor 42 and associated circuitry 62 are considered optional to implementation of the present invention. Digital processor 64 comprises any commercially available central processing unit or microcomputer. Once the appropriate heating value, density and/or percent gas inerts determination has been realized, using one of the above formulas, the determination is outputted to a communications interface 66, which includes display means 68 and storage means 70 capable of presenting for viewing and/or storing determined values for subsequent use. If desired, a regulation/control signal is outputted via line 72.

Figure 3:
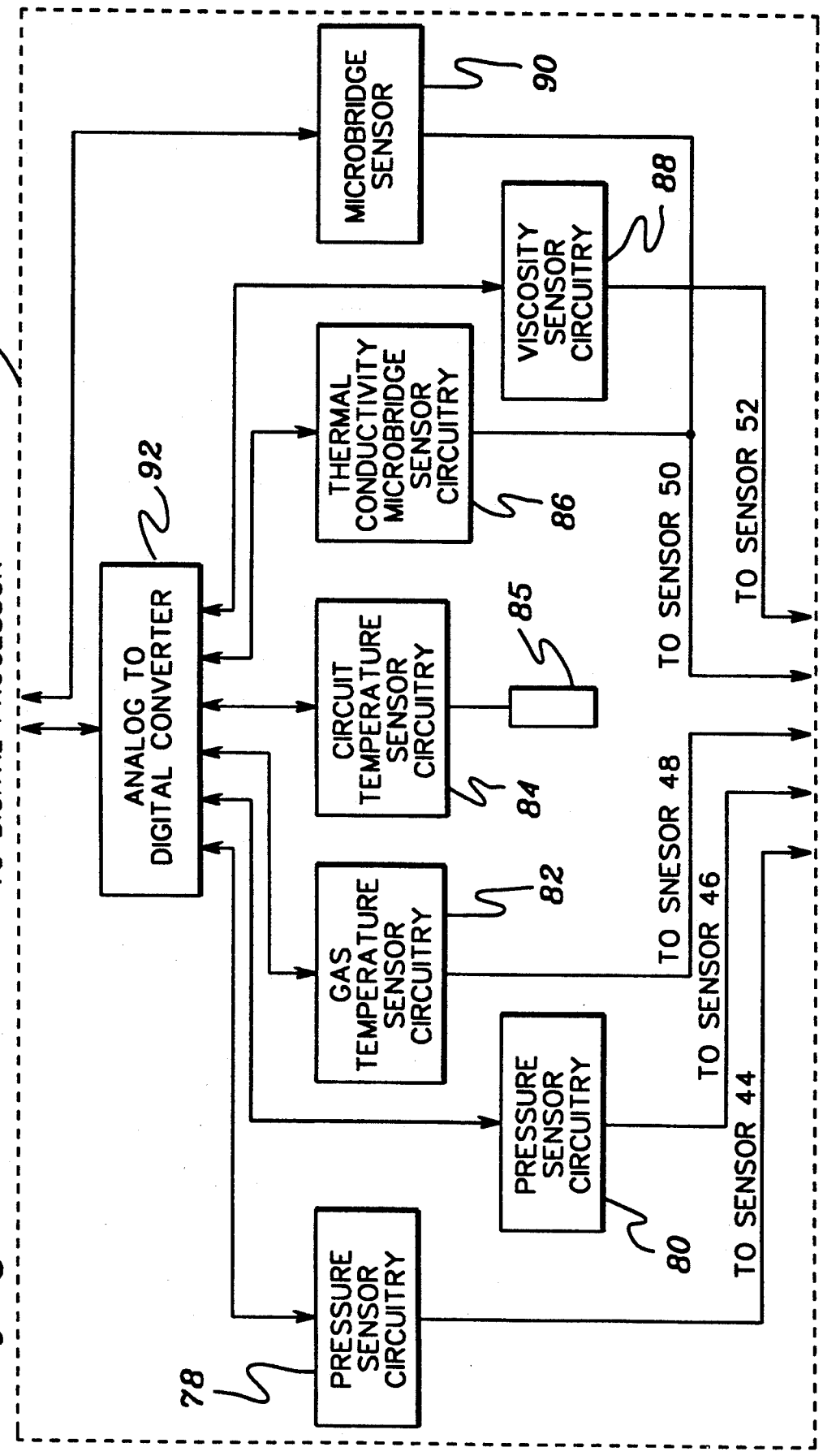
FIG. 3 is a block diagram of he analog circuit board depicted in FIG. 1.

Analog circuit board 58 is depicted in greater detail in FIG. 3.

As shown, circuit 58 includes pressure sensor circuitry 78 & 80, gas temperature sensor circuitry 82, circuit board temperature sensor circuitry 84 and temperature sensor 85, thermal conductivity microbridge sensor circuitry 86, and its microbridge driver 90, and viscosity sensor circuitry 88. Each sensor circuitry is electrically connected to the appropriate sensor and to an analog to digital converter 92. From converter 92, signals flow to processor 64 (FIG. 2).

In the embodiment depicted, pressure sensor circuitry 78 is connected to sensor 44, and pressure sensor circuitry 80 is connected to sensor 46. Circuitry 78 & 80 and sensors 44 & 46 each comprise any commercially available pressure sensor, such as that manufactured by Honeywell, Inc. of Bloomington, Minn. and marketed under Model No. ST3000. Temperature sensor circuitry 82 & 84 similarly comprise any well-known resistance temperature measurement apparatus such as a wheatstone bridge configuration wherein a change in the resistance branch exposed to the unknown temperature produces an unbalance proportional to said temperature. Circuitry 84 is connected to a sensor 85 which is positioned on analog circuit board 58. Circuitry 78, 80, 82 & 84 and their associated sensors are necessary in order to account for sensor and circuit non-linearities and influence of electronic temperature changes, e.g., on resultant thermal conductivity and viscosity measurements. Also, actual measurements can be converted by one of ordinary skill in the art from measured gas temperature and pressure values to corresponding values at standard temperature and pressure.

As noted above, there are numerous known techniques for determining thermal conductivity (and specific heat) of the fuel gas which could be implemented as sensor circuitry 86. However, applicant believes that a preferable approach is described in a recently issued patent entitled, "Measurement of Thermal Conductivity and Specific Heat," U.S. Pat. No. 4,944,035, the entirety of which is hereby incorporated herein by reference. This approach will now be described in detail with reference to FIGS. 4(a)-8.

With respect to measuring thermal conductivity in fluids, various types of detectors have been used. This includes resistance bridge type sensors. One such device is described in U.S. Pat. No. 4,735,082 in which thermal conductivity is detected using a wheatstone bridge technique in which a filament in one diagonal of the bridge is placed or positioned in a cavity through which the sample gas of interest is passed. The filament is used to introduce a series of amounts of thermal energy into the fluid of interest at alternating levels by varying the input voltage which, are, in turn, detected at the other diagonal as voltage difference signals. Integration of the changes of the value of the successive stream of signals yields a signal indicative of the heat dissipation through the fluid, and thus, the thermal conductivity of the fluid.

Further to the measurement of thermally induced changes in electrical resistance, as will be discussed in greater detail below, recently very small and very accurate "microbridge" semiconductor chip sensors have been described in which etched semiconductor "microbridges" are used as condition or flow sensors. Such sensors might include, for example, a pair of thin film sensors around a thin film heater. Semiconductor chip sensors of the class described are treated in a more detailed manner in one or more patents, such as U.S Pat. Nos. 4,478,076, 4,478,077, 4,501,144, 4,651,564 and 4,683,159.

It is apparent, however, that it has often been necessary to address the measurement of specific heat $c_p$, and thermal conductance, k, of a fluid of interest with separate and distinct devices. Not only is this quite expensive, it also has other drawbacks. For example, the necessity of separate instruments to determine specific heat and thermal conductivity may not allow the data consistency and accuracy needed for useful fluid process stream (gas or liquid) characterization. Further, the required degree of correlation may not be present. Because the determination of heat content as contemplated herein depends on both measurements, e.g., see equation (8) and Table I, this takes on even more importance.

The above-referenced U.S. Pat. No. 4,944,035 overcomes the many disadvantages associated with the determination of both specific heat, $c_p$, and thermal conductivity, k, by providing simple techniques which allow accurate determination of both properties in a sample of interest using a single sensing system. The approach contemplates generating an energy or temperature pulse in one or more heater elements disposed in and closely coupled to the fluid medium (gas or liquid) of interest. Characteristic values of k and $c_p$, of the fluid of interest then cause corresponding changes in the time variable temperature response of the heater to the pulse. Under relatively static sample flow conditions this, in turn, induces corresponding changes in the time-variable response of one or more temperature responsive sensors coupled to the heater principally via the fluid medium of interest.

The thermal pulse of a source need be only of sufficient duration that the heater achieves a substantially steady-state temperature for a short time. This pulse produces both steady-state and transient conditions at the sensor. Thermal conductivity, k, and specific heat, $c_p$, can be sensed within the same sensed thermal pulse by using the steady-state temperature plateau to determine k, which is then used with the rate of change of temperature in the transient condition to determine $c_p$. Both values then provide input to the determination of heat content, density or percent concentration of gas inerts.

The microbridge semiconductor chip sensor contemplated, for example, in certain embodiments preferred for the implementation of the thermoconductivity sensor may resemble the form of one or more of the microbridge systems illustrated in the patents identified above. Such a system is exemplified by the figures provided with U.S. Pat. No. 4,501,144. Reference should be made to said patent for a better understanding of the discussion to follow. While the present discussion is believed sufficient, to the extent necessary, additional material contained in the microbridge related patents cited is deemed to be incorporated herein by reference.

Figure 4A:
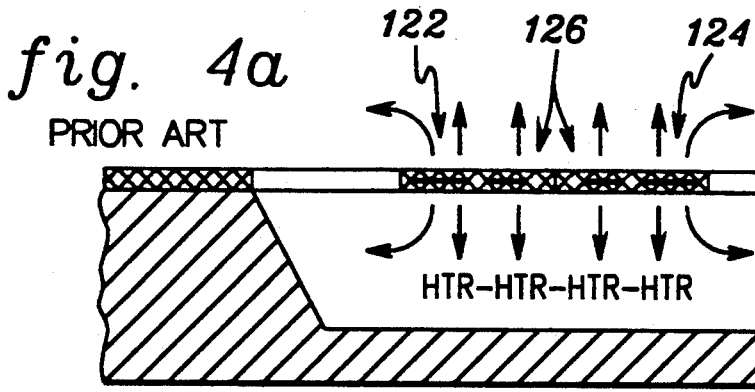
FIGS. 4(a), 4(b), and 4(c), represent several heater/sensor configurations of microbridge systems in accordance with applicant's preferred implementation of the present invention.
Figure 4B:
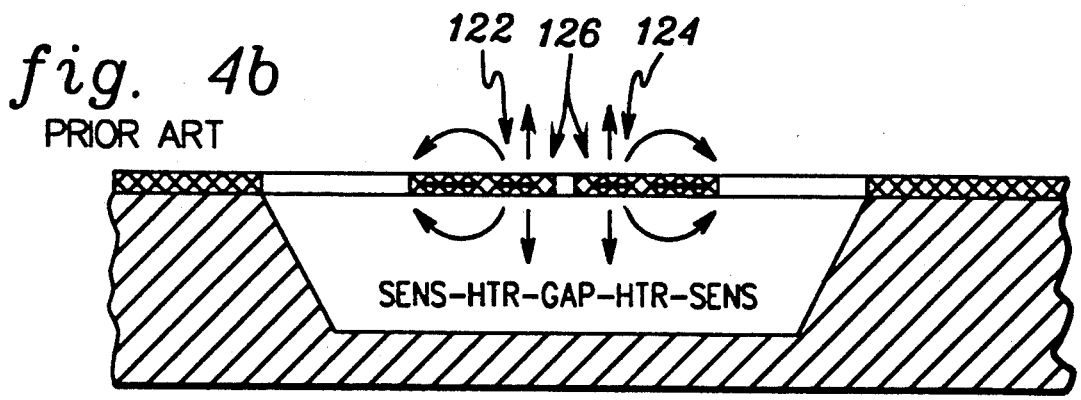
Figure 4C:
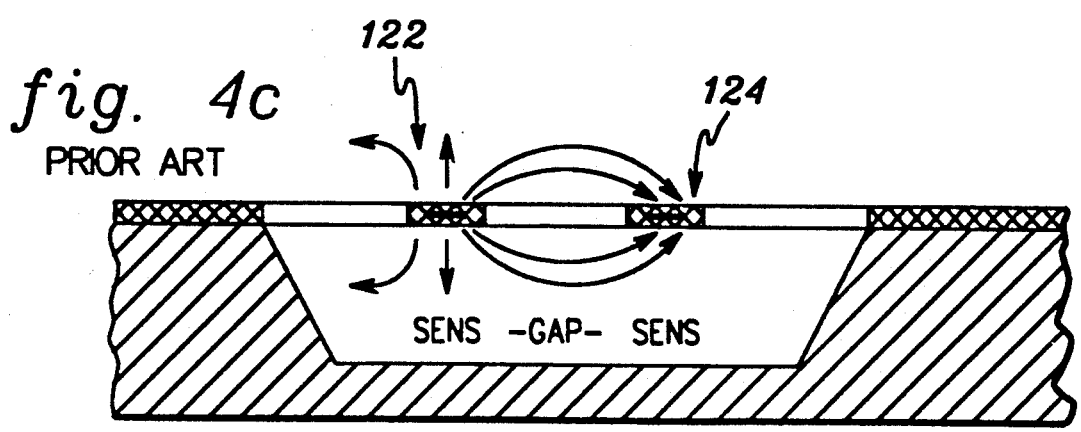

Now with reference to the implementation of the thermal conductivity sensor, FIGS. 4(a), 4(b) and 4(c), depict three slightly differing embodiments or configurations representative in terms of number and arrangement of the heaters and sensors which can be used in this structure. In FIG. 4(a), all of the elements 122, 124 and 126 are used as heaters. FIG. 4(b) is an embodiment in which the thin film element 126 acts as heater and elements 122 and 124 act as sensors. The embodiment of FIG. 4(c), represents the preferred arrangement in which the element 122 acts as heater and element 124 acts as sensor. The effective gap and thus the thermal isolation between heater and sensor is desirably wider in the embodiment of FIG. 4(c).

In the implementation of the applicant's preferred thermal conductivity sensor, particular attention is directed to (1) setting specific temperature markers in the sensor to determine the time periods needed for achieving the corresponding temperature changes, (2) using temperature sensors which are physically separated from the heater so that the direct influence of the heater and heat conducted to the sensor other than via the fluid of interest is reduced, and (3) using a pulse which reaches at least a momentary steady-state plateau to determine k, which then is used with the transient measure to determine $c_p$.

Figure 5:
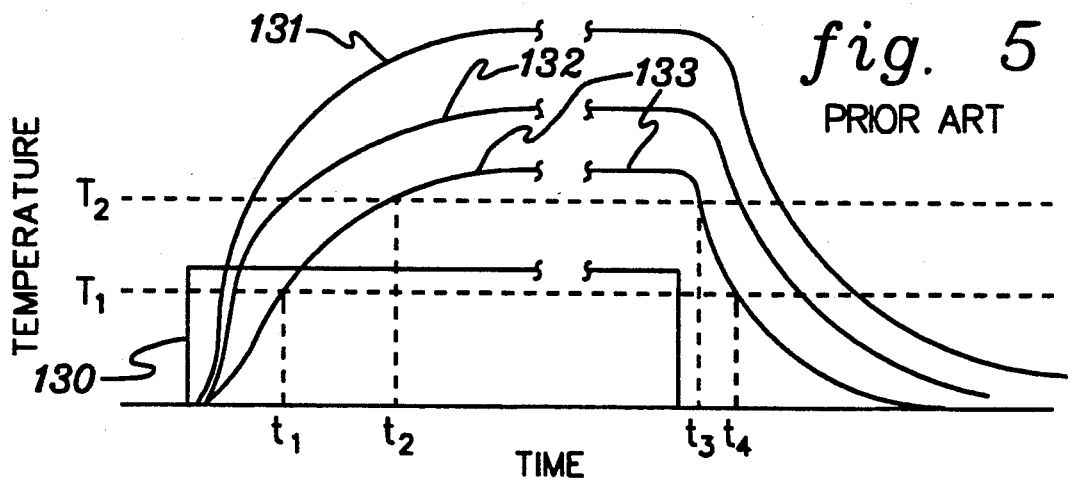
FIG. 5 is a schematic representation of sensor time/temperature response curves according to a heater pulse.

FIG. 5 graphically depicts a square wave electrical energy pulse 130 to the heater 126 which results in quasi square wave heat pulses released by the heater. These, in turn, result in reactive curves as at 131, 132 and 133 at the sensor which vary as described below. The pulse applied to the heater, for example, may have a height of about 4 volts with a pulse width of 100 ms. Since the heater is closely coupled through the fluid medium to the sensors, the family of curves 131, 132 and 133 resembles the shape of the input pulse 130. They show the heat response in the sensors 122 and 124. The curves generally include beginning and ending transient portions flanking a relatively steady-state central portion. The quick response of the sensor allows a relatively long steady-state to exist even with a pulse of 100 ms. Of course, the curves are affected by factors such as pressure and temperature as they influence the effective thermal conductivity and specific heat of the particular fluid of interest.

Heat flowing from the heater element or elements to the sensor element or elements is conducted both through the fluid and through the solid semiconductor element support substrate or the like. It is advantageous with respect to the measurement of k or $c_p$ of the fluid of interest that the amount of heat reaching the sensor through the solid connections be minimized so that substantially all the measured thermal effect is generated via the fluid of interest.

With respect to the transfer of heat to the sensor(s), some background information regarding the propagation of heat or temperature waves is presented. The speed of propagation, v, of a one dimensional wave (if it features an exponential decay profile) is constant and given by the expression:

$$v = D_T/a = (D_T/b)^{0.5}, \qquad (9)$$

where:
α = exponential decay constant,
b = rise time constant at a fixed location, and
$D_T$ = thermal diffusivity.

A complete list of nomenclature and subscripts with units appears in Table II, below. $D_T$ is related to k and $c_p$ by the expression:

$$D_T = k/c_p \qquad (10)$$

$D_T$, therefore, if known, may be a key to obtaining $c_p$. The rise time constant, b, was measured to be about 4 msec. For typical gases, $D_T$ ranges from 1.7 cm²/s for He to 0.054 cm²/s for $C_3H_8$. Metals exhibit high values such as 1.7, 1.1 and 0.18 cm²/s respectively for Ag, Cu and Fe. Insulators, however, are even lower than the gases at .004 cm²/s for glass and 0.0068 cm² for $Si_3N_4$ which, as discussed above, is a good insulator. The propagation speed, v, in a typical gas sample then is about $(1/0.004)^{0.5} = 15$ cm/s. This compares with $(0.0068/0.004)^{0.5} = 1.3$ cm/s for $Si_3N_4$, assuming that the same rise time constant of about 4 ms is applicable to both the one measured in the $Si_3N_4$ and the actual one in the gas.

The effect is that the influence of the temperature wave propagating from one thin film strip, that is, the heater, to a second thin film strip, the sensor, both being embedded in a membrane of $Si_3N_4$, since it reduces the contribution of heat flow through the solid media. This is beneficial to the accuracy of the system.

Typical microbridge embodiments are illustrated by FIGS. 4(a)–4(c). They will now be explained in greater detail.

The configuration of FIG. 4(a) involves using the same microresistance 122, 124, 126 for the heating pulse and the sensing task. In this embodiment, the resistive heater-sensor element may be one leg of a conventional resistive wheatstone bridge in a control circuit.

TABLE II

| Symbol | NOMENCLATURE | Units |
|---|---|---|
| α | Exponential Decay Constant | cm |
| $a_1 a_m$ | Constant | |
| A | Optical Absorption | |
| B | Area of Heat Transfer to Microbridge or to Gas | cm² |
| b | Rise Time Constant at a Fixed Location | °C./s |
| $c_p$ | Specific Heat | cal/(cm³ °C.) |
| $D_t$ | Thermal Diffusivity, $D_T = k/c_p$ | cm²/s |
| $H_c$ | Heat Content of Gas | MJ/m³ |
| K | Thermal Conductivity | cal/(sm °C.) |
| L | Length of Thermal Conductance Path in Gas or Solid | cm |
| M | Molecular Weight of Gas | grams/mole |
| n | Viscosity of Gas | µpoise |
| P | Pressure of Gas | psia |
| ρ | Density of Gas | grams/cm³ |
| Q | Power of Heat Release Rate | watts |
| $R_o$ | Resistance at Room Temperature | ohms |
| t | Time | s |
| T | Absolute Temperature | °C. |
| U | Bridge Output or Amplified Bridge Output | V |
| V | Volume of Gas or Solid (Microbridge) | cm³ |
| v | Speed of Propagation | cm/s |
| x | Temperature coefficient of resistance | °C.¹ |
| SUBSCRIPTS | | |
| c | Conduction | |
| s | Microbridge or Solid | |
| g | Gas | |
| o | Room, Reference or Gas Temperature | |

TABLE II-continued

| Symbol | NOMENCLATURE | Units |
|---|---|---|
| | Without Microbridge Heating | |
| h | Heater or Hot | |
| m | Middle or Medium | |
| tl–ti | n, A, k or $c_p$ at various temperatures | |

FIG. 4(b) depicts an arrangement wherein the center microresistance structure 126 is used as a heater flanked by two symmetrically located outer sensing resistance elements 122 and 124. The elements 122 and 124 are separated from the heater 126 by a narrow gap.

FIG. 4(c) shows an embodiment configuration in which the left element of the bridge 122 is used as the heating element and the right element 124 as the sensor. This embodiment takes advantage of a rather large central gap to achieve improved thermal isolation between the heater and the sensor.

Figure 6:
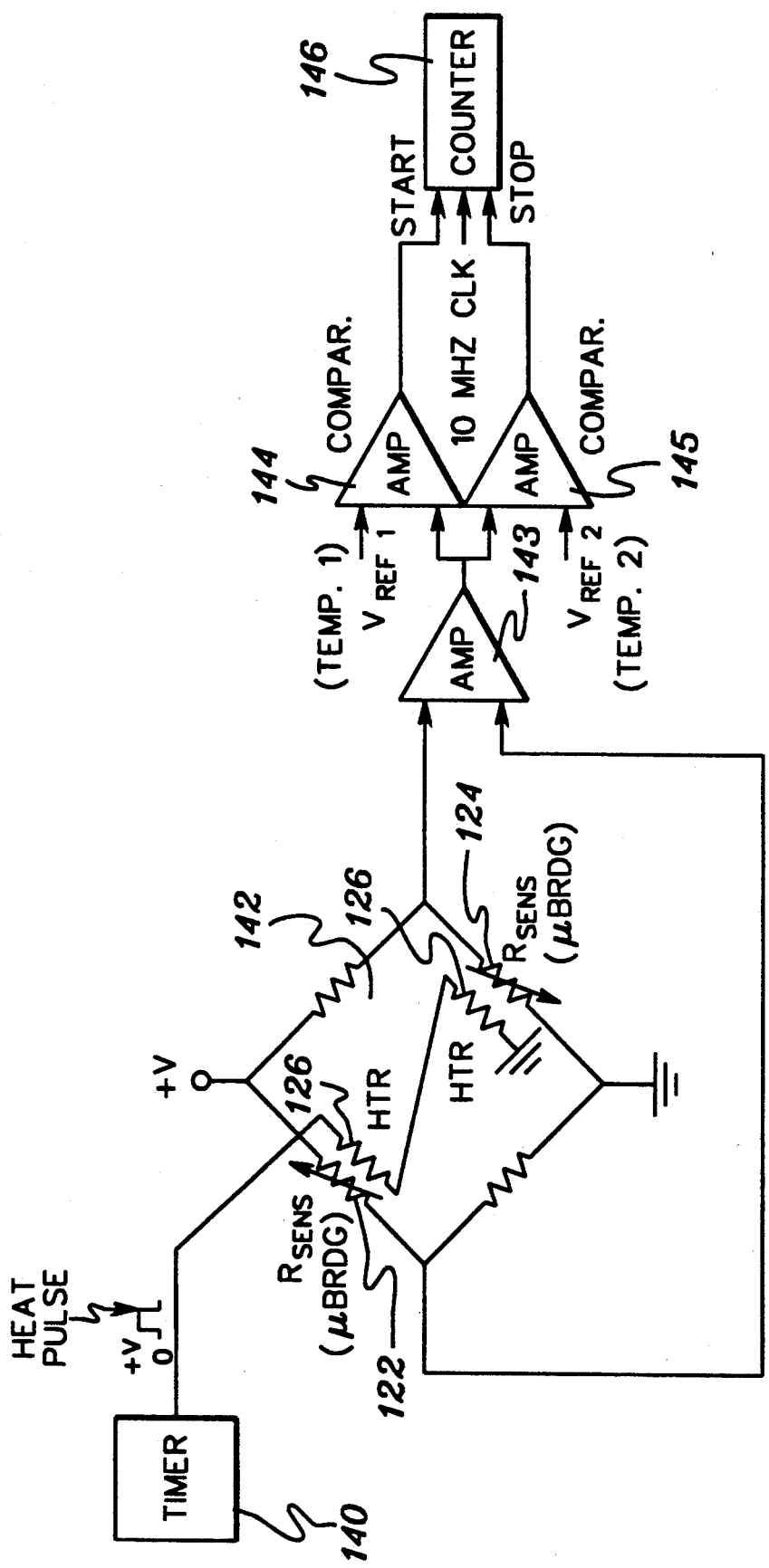
FIG. 6 is a partial schematic and block diagram of a circuit for use with a sensor as depicted in FIG. 4(b) in accordance with the preferred implementation.

FIG. 6 shows a modified control circuit which uses the center microresistance 126 as heater, while the sensing task is performed by the two resistors 122 and 124. The dual heater sensor configuration corresponds to FIG. 4(b) and the circuit is representative of a typical sensor/measurement circuit. FIG. 6 includes a timer 140 providing square-wave electrical pulses to the heater 126. The heater couples the heat pulse to the sensors 122 and 124 in the bridge 142. The output of the bridge is connected through an amplifier 143 to a pair of comparators 144 and 145 which operate "start" and "stop" inputs to a counter 146 which counts 10 mHz clock pulses. The counter counts measure the time interval $(t_2 - t_1)$ between temperatures $T_2$ and $T_1$ illustrated in FIG. 5.

Figure 7B:
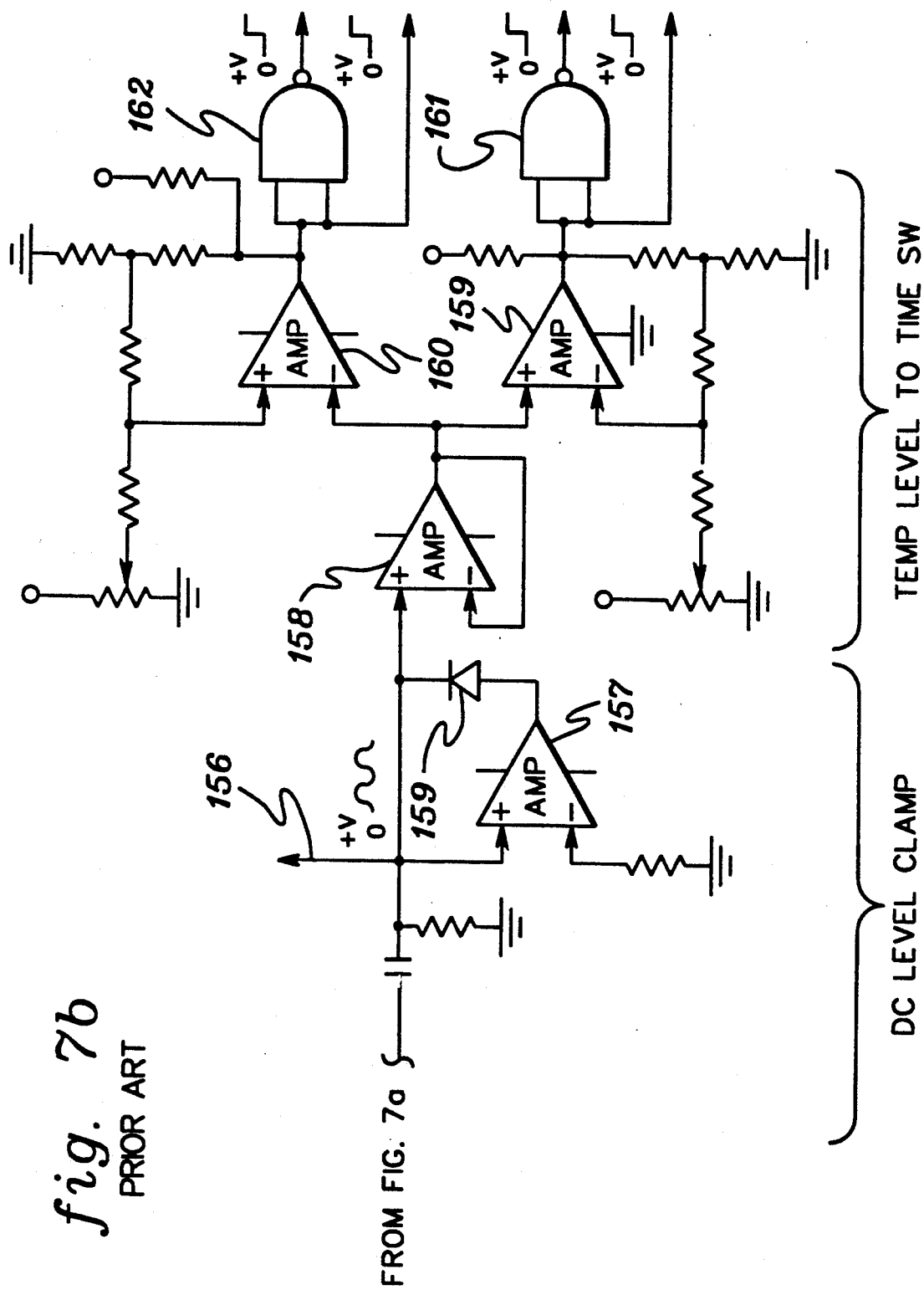

FIG. 7 is similar to FIG. 6 but more detailed. The bridge configuration is the heater-space-sensor configuration of FIG. 4(c). The sensor resistance arm of the microbridge is set into a wheatstone bridge 150 at 124. Another proximate resistive arm 122 is fed a voltage pulse from pulse generator 151 to provide a heat pulse into the microbridge element 126. The wheatstone bridge 150 also may contain a nulling balancing resistor 152 which can be used to initially zero the device. The microbridge resistor sensor 124 in the wheatstone bridge receives the heat pulse from heater element 122 principally by thermal conduction through the surrounding fluid. Some conduction, of course, does occur through the solid microbridge substrate and surroundings.

The circuitry of FIG. 7 is conventional and can readily be explained with reference to its functional operation with regard to processing the bridge output signal. The voltage output signals of the bridge 150 are amplified by differential amplifiers 153 and 154 in a differential amplifier section. The imbalance signal is further amplified by a high gain amplifier at 155. The signal at 156 is in the form of a DC voltage signal, U, the amplitude of which is solely related to the thermal conductivity of the fluid of interest.

The remainder of the circuitry of FIG. 7 includes a DC level clamping amplifier 157 and isolation amplifier 158. The temperature level, time-related switching and counting circuitry includes comparators 159 and 160 together with NAND gates 161 and 162 having outputs which are connected to the counter timing device (not shown) as in FIG. 6. By measuring the time needed for the sensor temperature to rise or fall between two or more known temperature values or markers as represented by sensor resistance or bridge voltage outputs, a measure related to the specific heat per unit volume, $c_p$, of the fluid of interest is obtained. The timing device may be a conventional 10 MHz pulse counter or the like. Again, this is illustrated schematically in FIG. 5.

The output signal from the wheatstone bridge, U, represents the voltage imbalance caused by the temperature change in microbridge sensor or sensors induced by the corresponding heater pulse output. Because the magnitude of this imbalance is related directly to the amount of energy absorbed by the sensor or sensors, the amplitude of the signal is directly related to the thermal conductivity, k, of the conducting media in a manner next explained.

FIG. 5 shows that during much of the about 100 ms wide pulse period, the temperature of the sensor reaches and maintains a constant value. During this time, the influence of the energy sink or source terms represented by specific heat are zero, which means that only thermal conductivity governs the value of the sensor temperature.

The literature value of the thermal conductivity of several gases was compared with the measured sensor temperature expressed directly in terms of the measured wheatstone bridge and balance potential, U. This relationship was derived empirically for a microbridge of the type depicted in FIG. 4(c) using the least squares method in a multiple regression analysis to achieve a best fit curve. This relation can be linearized over a modest span sufficient for the purpose of the sensor. Other combination configurations of heater/sensor embodiments can likewise be calibrated using known gases or gases of known k. Thus, using an off the shelf flow sensor of the type of FIG. 4(c) in the circuit of FIG. 7, a 4 volt pulse of 100 ms duration was used.

This yielded an approximate linear relationship between U and $k_g$ of the form:

$$k_g = a_4 U + a_5 \tag{10a}$$

The linear approximation holds over enough of a span to provide accurate measurements. Similar relations may be derived under other measurement conditions including additional pressure correction terms.

Further details related to determining the coefficients for the algorithms to compute $c_p$ are described next. This determination requires that the measuring system be calibrated first, which consists of determining the coefficients $a_1$, $a_2$, and $a_3$, of the algorithm to the computer $c_p$.

Assuming a two-dimensional model for heat transfer in the microbridge, see FIGS. 4(a)-4(c), the measured sensor temperature response may be described with reference to the following processes (at zero gas flow):
1) Heat release by the heater element film;
2) Temperature build up in the heater element material (FeNi or Pt) and surrounding support material (insulator $Si_3N_4$), i.e. within the bridge material;
3) Conduction towards the sensor via a) the bridge material, and b) the fluid phase surrounding the bridge;
4) Temperature build up in the sensor material (as in heater material in item 2 above), and in the gas surrounding it by the heat arriving via the above processes;
5) Achieving a steady-state distribution of temperature; and
6) The reverse process to steps 1-5 during the start of the heater off-period.

Further assuming, for the sake of simplicity, that the specific heats of the involved gaseous and solid materials do not depend on temperature, we can approximately describe the above processes by the following expressions (see Table II above for symbol explanation) using the same process numbering as above:
1) $Q = V^2/(R_o(1 + \alpha(T_h - T_o)))$ for small temperature rises.
2) The heater temperature results from balancing the heat input and output rates: $T_h - T_o = Q/(k_s B_s/L_s + k_g B_g/L_g)$ with Q in watts; the temperature $T_h$ is established in a time that is short compared to the time it takes to reach the sensor if the sensor is not identical to the heater, as in configurations 4(b) and 4(c).
3) In a truly one-dimensional case most of the released power Q eventually arrives at the sensor, since it only has two ways to go (+x and −x directions). In a two- (or even three-) dimensional case a major part of Q gets dissipated in the y and z directions, so that only a fraction, $Q_c$, is conducted to the sensor, with a corresponding drop of the original temperature, $T_h$ down to an intermediate temperature $T_m$. The sensor then experiences an energy rate arrival of $$Q_c = (T_m - T_o)(k_s B_s/L_s + k_g B_g/L_g) \tag{11}$$

4) The sensor temperature rise rate is governed by the specific heat of the gas surrounding the sensor and the closely coupled material of the sensor itself so that:

$$Q_c = (dT/dt) c_{ps} V_s + (dT/dt) c_{pg} V_g \tag{12}$$

It is readily apparent from equation (12) that $c_{pg}$ could be determined for an unknown gas if the various quantities entering in equations (11) and (12) were either known or measurable. It has been found, however, that even if only dt, dT, $T_o$, P and $k_g$ are conveniently measurable, the other quantities may be determined by calibration. This can be done as follows:

For calibration, gases of known composition (preferably but not necessarily pure), and therefore of known specific heat and thermal conductivity at the used pressure and temperature (both also measured), are brought in contact with the sensor. The effect of the pulsed heat releases is recorded in terms of the lapsed time, $t_2 - t_1$ as has been described. After noting results for various gases, pressures, heater temperatures and/or heating-/cooling periods, with pulses of constant temperature, voltage, current or power, the recorded time and condition data are entered into an array of data ports which can be used for automatic or computerized data processing or other number crunching techniques.

The process can be illustrated with the help of equations (11) and (12), by way of example, without excluding other, similar approaches likely to occur to one skilled in numerical analysis. With this in mind, the following ports receive data or input for various gases, pressures (and temperatures):

| Ports: | Y | X1 | X2 |
|---|---|---|---|
| Inputs: | $c_{pg} P/P_o$ | $(t_2-t_1)k_g$ | $t_2-t_1$ |

A known and available multiple linear regression analysis (MLRA, see FIG. 8) program can determine the linear coefficients $a_1$, $a_2$, and $a_3$ (e.g., by matrix inversion), which, together with the above input data, forms the calibrated expression derived from equations (11) and (12) to compute specific heat, $c_p$:

$$c_{pg} P/P_o = a_1(t_2-t_1) k_g + a_2(t_2-t_1) - a_3 \quad (13)$$

The determined (calibration) coefficients, of course, represent the lumped factors of several sensor properties or conditions from equations (13) and (14):

$$a_1 = (T_m - T_o)(B_g/L_g)(V_g dT),$$

$$a_2 = (T_m - T_o)(B_g/L_s)(V_g dT)k_s \quad (14)$$

$$a_3 = c_{ps} V_s / V_g$$

In order to minimize differences in $T_m$ at the sensor location, the most advantageous operation from among constant temperature, voltage, current or power is chosen. The above method is demonstrated on the basis of 1) constant voltage pulses, which result in quasi square wave heat pulses released by the heater, and 2) changes in gas type ($CH_4$, $C_2H_6$, air and $O_2$) and pressure; the chosen configuration was 4(b).

The $dt = t_2 - t_1$ and pressure data for each of the gases used were obtained, for which the $c_p$ and k values can be obtained from the open literature. This relation is linearized by applying the least squares method in a multiple linear regression analysis to achieve the best fit line. After entering these data into the above ports Y, X1 and X2, the regression analysis program was performed. The obtained result was, for a configuration as in FIG. 4(b):

$$a_1 = `16509, a_2 = 3.5184 \text{ and } a_3 = 0.005392 \quad (15)$$

The final step in using this calibration method involves known means to store, write or burn in the obtained, tailored values of $a_1$, $a_2$ and $a_3$ for the individual microbridge, which may be a Honeywell MICRO-SWITCH Model No. AWM-2100V, into the memory linked to it. The microsensor is then ready for use to measure the specific heat of unknown gases, provided that P and k be known at the time of measurement.

Figure 8:
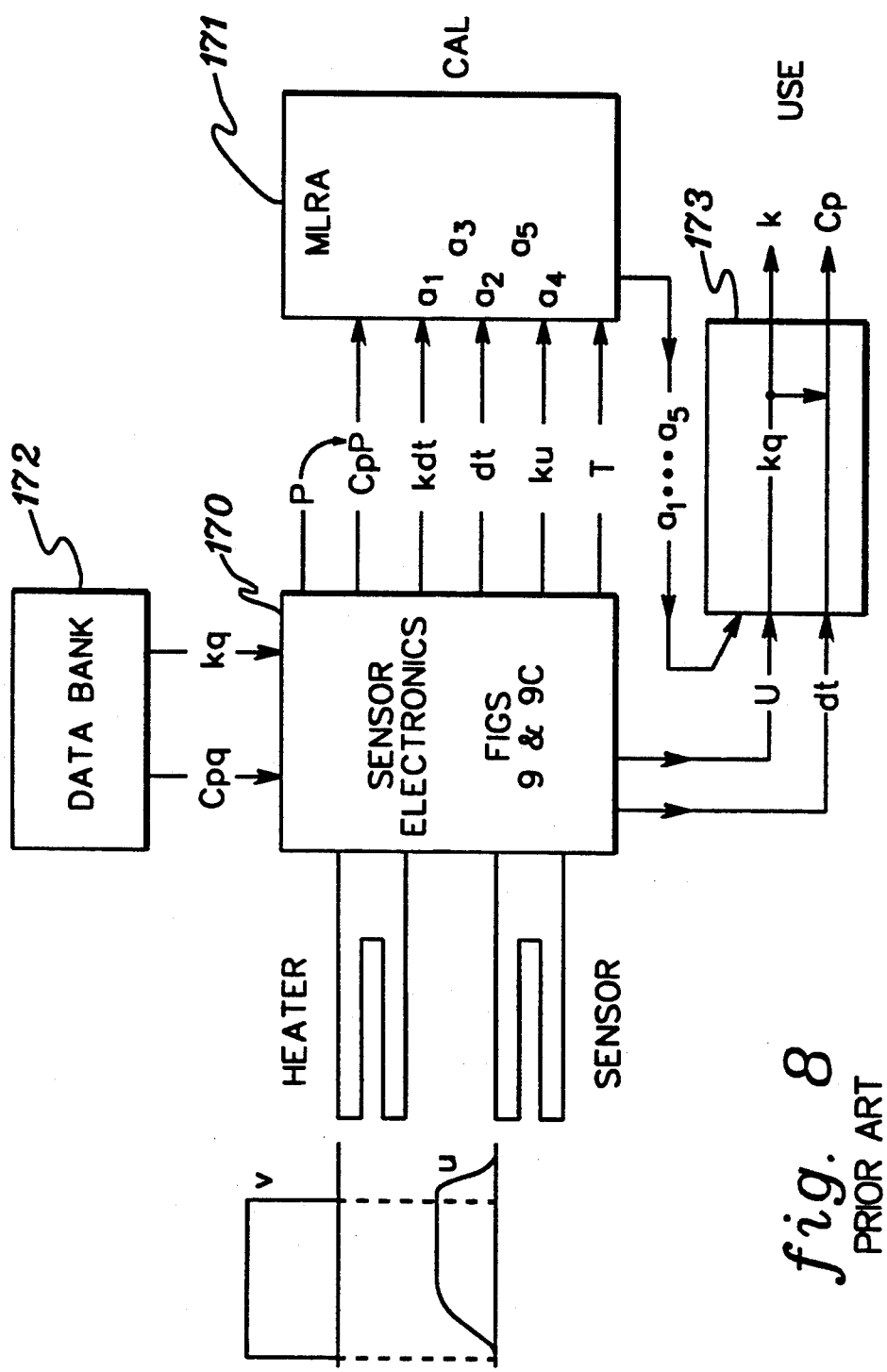
FIG. 8 is a schematic block diagram of the preferred thermal conductivity sensor embodiment including calibration and use functions.

FIG. 8 depicts a schematic block diagram of a device for measuring $c_p$ and k. The system includes the signal processing circuitry indicated by 170, a multiple linear regression analysis (MLRA) unit 171 for deriving the known equation constants for the particular microbridge configuration and circuitry used, i.e., $a_1$-$a_n$, a data bank 172 for storing calibration $c_p$ and k data and an output interface unit 173.

With respect to the embodiment of FIG. 8, prior to use, field recalibration may be accomplished simply by entering the P, $c_p$ and k values of the test gas into the data bank. If P cannot be measured independently of the sensor already in the subject system its errors can be incorporated as a correction in the $c_p$ and k calibration. The measured values of U and dt are then used as in the measurement mode to determine sensor values of k and $c_p$. If they disagree from the entered values the constants $a_3$ and $a_5$ may be modified to fit the entered or book values.

This approach may be a practical one for field use, but it should be checked by using a second test gas. If that agrees, the recalibration may be completed. If not, a complete calibration of all $a_1$-$a_5$ coefficients should be made.

It should be mentioned that in all of the above discussion the influence of temperature was not mentioned for the sake of simplicity. It is well known, however, that temperature does influence both $c_p$ and k, but can be addressed, if necessary, in one of the following ways:
1) Controlled, (expensive and energy consuming) or
2) Compensated by special temperature-sensitive elements in the analog part of the circuit, or
3) Entered into the sensor algorithm as an additional parameter, which is sensed, e.g., by monitoring one of the many available temperature dependent resistors on the sensor. This is the preferred approach for sensing systems requiring maximum accuracy.

With respect to use of the instrument of FIG. 8, the U and $dt = t_2 - t_1$ (and P) signals obtained for an unknown gas are processed as follows in this mode:
1) Computation of k from expression (3) using the coefficients $a_4$ and $a_5$ which have been stored in (or burned into) the sensor's memory after calibration, and
2) Computation of $c_p$ from expression (6). It should also be noted that a pressure signal is also needed as a basic ingredient since $c_p$ is used here in relation to a volume of gas as opposed to k which is largely pressure independent if the sensor is used at or above atmospheric pressure, at which the gas mean free path is small compared to the characteristic dimensions of the involved sensor.

As noted above, the thermal conductivity and specific heat microsensor just described comprises applicant's preferred arrangement for obtaining said measurements. However, the appended claims should not be read so narrowly, but, rather, should be read to encompass any known means for determining gas thermal conductivity and gas specific heat.

Now returning to FIG. 3, and as noted above, several techniques are available in the open literature for ascertaining fuel gas viscosity. For example, circuitry 88 and sensor 52 could be implemented as a flowing gas capillary-type arrangement. (However, sensor 52 would need to be moved from area 56 to a flowing gas environment within chamber 36.) Preferably, the novel approach described in the above referenced copending application entitled "Multiple Gas Property Sensor" is used to ascertain the viscosity of the fuel gas. Briefly described, this approach utilizes the frequency change and series resistance change of a crystal resonator positioned within the fuel gas to determine both pressure and the combined term molecular weight multiplied by viscosity (or, alternatively, density multiplied by viscosity). Using this approach, sensor circuitry 80 and sensor 46 could be eliminated since the process described in said copending application produces an absolute pressure reading, which is used for correction of measured viscosity and molecular weight. For a more complete understanding of this approach, reference should be made to said case.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

What is claimed is:

1. An electronic apparatus for the combustionless determination of the quality of gaseous fuel fed to gas consumption devices, said apparatus comprising:
   a sensor chamber having a plurality of sensors therein;
   means for conducting at least a partial stream of a fuel gas through the sensor chamber such that said gas is in contact with said plurality of sensors;
   first means for generating a first electrical signal at one of said plurality of sensors, said first electrical signal being representative of a first fuel gas quality, said first fuel gas quality comprising one of thermal conductivity, specific heat, viscosity and optical absorption of said fuel gas;
   means for transferring said first electrical signal to a computer;
   second means for generating a second electrical signal at one of said plurality of sensors, said second electrical signal being representative of a second fuel gas quality, said second fuel gas quality comprising one of said thermal conductivity, specific heat, viscosity and optical absorption fuel gas qualities, said second gas quality comprising a different one of said fuel gas qualities than said first gas quality;
   means for transferring said second electrical signal to said computer; and
   means, using said computer, for periodically generating signals using the first and second generated electrical signals as a measure for both the heat content and percent gas inerts of the fuel gas, each according to the formula:

$$\mu = a_0 + b_1 x^{m1} + c_1 y^{p1}$$

where:
$\mu$ = one of said fuel gas heat content and percent concentration of gas inerts,
$a_0, b_1, c_1,$ = constants,
$m1, p1,$ = exponents,
x = signal representative of the first fuel gas quality,
y = signal representative of the second fuel gas quality, and
+ = one of addition, subtraction, multiplication and division.

2. The apparatus according to claim 1, further comprising:
   one of a display means and a recording means; and
   means for transmitting said computer generated signals to said one of display means and recording means.

3. The apparatus according to claim 1, wherein said first fuel gas quality and said second fuel gas quality are sensed at a first temperature, and said apparatus further comprises:
   means for modifying the temperature at at least one of said plurality of sensors;
   third means for generating a third electrical signal representative of the second fuel gas quality at said second temperature;
   means for conducting said third electrical signal to the computer; and
   said computer signal generating means including means for using said first, second and third electrical signals to determine the heat content and percent gas inerts of the fuel gas according to the formula:

$$\mu = a_0 + b_1 x_{t1}^{m1} + c_1 y_{t1}^{p1} + c_2 y_{t2}^{p2}$$

where:
$\mu$ = said one of said fuel gas heat content percent concentration of gas inerts,
$a_0, b_1, c_1, c_2$ = constants,
$m1, p1, p2$ = exponents,
$x_{t1}$ = signal representative of the first fuel gas quality at temperature t1,
$y_{t1}$ = signal representative of the second fuel gas quality at temperature t1, and
$y_{t2}$ = signal representative of the second fuel gas quality at temperature t2.

4. The apparatus according to claim 3, wherein in said formula of said computer signal generating means:

$$x_{t1} = f(n)$$

$$y_{t1} = f_1(k_{t1}, k_{t2})$$

$$y_{t2} = f_2(k_{t1}, k_{t2})$$

where:
n = viscosity of the fuel gas,
$k_{t1}$ = thermal conductivity of the fuel gas at said first temperature t1,
$k_{t2}$ = thermal conductivity of the fuel gas at said second temperature t2,
f(n) = function of fuel gas viscosity,
$f_1(k_{t1}, k_{t2})$ = first function of fuel gas thermal conductivity at the first temperature, t1, and thermal conductivity at the second temperature, t2, and
$f_2(k_{t1}, k_{t2})$ = second function of fuel gas thermal conductivity at the first temperature, t1, and thermal conductivity at the second temperature, t2.

5. The apparatus according to claim 4, where in said computer signal generating means formula:
   $f(n) = d_1/n, d_1$ = constant;
   $f_1(k_{t1}, k_{t2}) = k_{t1}$; and
   $f_2(k_{t1}, k2) = k_{t2}/k_{t1}$.

6. The apparatus arrangement according to claim 1, further comprising:
   third means for generating a third electrical signal at one of said plurality of sensors, said third electrical signal being representative of a third fuel gas quality, said third gas quality comprising a different one of said thermal conductivity, specific heat, viscosity and optical absorption fuel gas qualities than said first gas quality and said second gas quality;
   means for conducting said third electrical signal to said computing means; and
where:
   said computer signal generating means uses a formula of the form:

$$\mu = a_0 + b_1 x^{m1} + c_1 y^{p1} + d_1 z^{q1}$$

where:
$\mu$ = said fuel gas heat content or percent concentration of gas inerts,
$a_0, b_1, c_1, d_1$ = constants,
$m1, p1, q1$ = exponents,
x = signal representative of said first fuel gas quality,
y = signal representative of said second fuel gas quality, and
z = signal representative of said third fuel gas quality.

7. The apparatus according to claim 1, wherein at least one of said quality of sensors comprises a microsensor and said apparatus further comprises means for obtaining substantially zero gas flow surrounding said microsensor within said chamber.

8. The apparatus according to claim 7, wherein said sensor chamber includes a gas inlet and a gas outlet and wherein said means for obtaining substantially zero gas flow within said chamber adjacent said sensors comprises at least one flow restricting screen positioned within said sensor chamber between said sensor and said gas inlet and outlet.

9. The apparatus according to claim 8, wherein said first electrical signal generating means and said second electrical signal generating means utilize at least one mass air flow sensor.

10. The apparatus according to claim 9, wherein said first electrical signal generating means and said second electrical signal generating means utilize at least one microbridge sensor.

11. An apparatus for the combustionless measurement of the quality of gaseous fuel fed to gas consumption devices, said apparatus comprising:
- a sensor chamber having a plurality of sensors therein;
- means for conducting at least a partial stream of a fuel gas through the sensor chamber such that said gas is in contact with said plurality of sensors;
- first means for generating a first electrical signal at one of said plurality of sensors, said first electrical signal being representative of one of the molecular weight and density of said fuel gas;
- means for transferring said first electrical signal to a computer;
- second means for generating a second electrical signal at one of said plurality of sensors, said second electrical signal being representative of the viscosity of said fuel gas;
- means for transferring said second electrical signal to said computer;
- third means for generating a third electrical signal at one of said plurality of sensors, said third electrical signal being representative of the thermal conductivity of said fuel gas;
- means for transferring said third electrical signal to said computer;
- fourth means for generating a fourth electrical signal at one of said plurality of sensors, said fourth electrical signal being representative of the specific heat of said fuel gas;
- means for transferring said fourth electrical signal to said computer; and
- means, using said computer, for periodically generating signals using the first, second, third and fourth generated electrical signals as a measure for both the heat content and percent gas inerts of the fuel gas according to the formula:

$$\mu = a_o + b_1\{(n)(z)\}^{o1} + c_1 k^{m1} + d_1 c_p^{p1}$$

where:
$a_o, b_1, c_1, d_1$ = constants,
$o1, m1, p1$ = exponents,
$n$ = viscosity,
$z$ = molecular weight, M, or density, $\rho$, of the fuel gas,
$k$ = thermal conductivity, and
$c_p$ = specific heat.

12. The apparatus according to claim 11, wherein the fuel gas comprises natural gas and when the first, second, third and fourth electrical signals are used by said computer signal generating means as a measure of the heat content of the gas, and the combined term viscosity multiplied by fuel gas molecular weight is used in said formula, then:
$a_o \approx -1287.7$
$b_1 \approx -0.00090189$
$o1 \approx 1.7514$
$c_1 \approx 1,048,800$
$m1 \approx -1.7142$
$d_1 \approx 808,700$
$p1 \approx 0.73846$.

13. An electronic apparatus for the combustionless determination of the quality of gaseous fuel fed to gas consumption devices, said electronic apparatus comprising:
- a sensor chamber having a plurality of sensors therein;
- means for conducting at least a partial stream of a fuel gas through the sensor chamber such that said gas is in contact with said plurality of sensors;
- first means for generating a first electrical signal at one of said plurality of sensors, said first electrical signal being representative of a first fuel gas quality, said first fuel gas quality comprising one of thermal conductivity, specific heat, viscosity and optical absorption of said fuel gas;
- means for transferring said first electrical signal to a computer;
- second means for generating a second electrical signal at one of said plurality of sensors, said second electrical signal being representative of a second fuel gas quality, said second fuel gas quality comprising one of said thermal conductivity, specific heat, viscosity and optical absorption fuel gas qualities, said second gas quality comprising a different one of said fuel gas qualities than said first gas quality;
- means for transferring said second electrical signal to said computer;
- means for selecting the gaseous fuel quality to be determined from one of the heat content, density and percent gas inerts of the fuel gas; and
- means, using said computer, for periodically generating signals using the first and second generated electrical signals as a measure for the selected gaseous fuel quality according to the formula:

$$\mu = a_o + b_1 x^{m1} + c_1 y^{p1}$$

where:
$\mu$ = said selected one of said fuel gas heat content, density and percent concentration of gas inerts,
$a_o, b_1, c_1,$ = constants,
$m1, p1,$ = exponents,
$x$ = signal representative of the first fuel gas quality,
$y$ = signal representative of the second fuel gas quality, and
$+$ = one of addition, subtraction, multiplication and division.

14. An electronic apparatus for the combustionless determination of the quality of gaseous fuel fed to gas consumption devices, said apparatus comprising:
- a sensor chamber having a plurality of sensors therein;
- means for conducting at least a partial stream of a fuel gas through the sensor chamber such that said gas is in contact with said plurality of sensors;
- first means for generating a first electrical signal at one of said plurality of sensors, said first electrical signal being representative of a first fuel gas quality, said first fuel gas quality comprising viscosity;

means for transferring said first electrical signal to a computer;

second means for generating a second electrical signal at one of said plurality of sensors, said second electrical signal being representative of a second fuel gas quality, said second fuel gas quality comprising thermal conductivity;

means for modifying the temperature at at least one sensor of said plurality of sensors;

third means for generating a third electrical signal representative of the second fuel gas quality at said second temperature;

means for conducting said third electrical signal to the computer; and means, using said computer, for periodically generating a signal using the first, second and third generated electrical signals as a measure for at least one of the heat content and percent gas inerts of the fuel gas according to the formula:

$$\mu = a_o + b_1 f(n)^{m1} + c_1 f_1(k_{t1}, k_{t2})^{p1} + c_2 f_2(k_{t1}, k_{t2})^{p2}$$

where:

$\mu$ = one of said fuel gas heat content and percent concentration of gas inerts, $a_o, b_1, c_1$ = constants, m1, p1, p2 = exponents, n = viscosity of the fuel gas, $k_{t1}$ = thermal conductivity of the fuel gas at said first temperature t1, $k_{t2}$ = thermal conductivity of the fuel gas at said second temperature t2, f(n) = function of fuel gas viscosity, $f_1(k_{t1}, k_{t2})$ = first function of fuel gas thermal conductivity at the first temperature, t1, and thermal conductivity at the second temperature, t2, and $f_2(k_{t1}, k_{t2})$ = second function of fuel gas thermal conductivity at the first temperature, t1, and thermal conductivity at the second temperature, t2.

15. An electronic apparatus for the combustionless determination of the quality of gaseous fuel fed to gas consumption devices, said apparatus comprising:

a sensor chamber having a plurality of sensors therein;

means for conducting at least a partial stream of a fuel gas through the sensor chamber such that said gas is in contact with said plurality of sensors;

first means for generating a first electrical signal at one of said plurality of sensors, said first electrical signal being representative of a first fuel gas quality, said first fuel gas quality comprising viscosity of said fuel gas;

means for transferring said first electrical signal to a computer;

second means for generating a second electrical signal at one of said plurality of sensors, said second electrical signal being representative of a second fuel gas quality, said second fuel gas quality comprising thermal conductivity;

means for modifying the temperature at at least one of said plurality of sensors;

third means for generating a third electrical signal representative of the second fuel gas quality at said second temperature;

means for conducting said third electrical signal to said computer; and means, using said computer, for periodically generating a signal using the first, second and third generated electrical signals as a measure for at least one of the heat content and percent gas inerts of the fuel gas according to the formula:

$$\mu = a_o + b_1(d^1/n)^{m1} + c_1 f_1(k_{t1})^{p1} + c_2 f_2(k_{t2}/k_{t1})^{p2}$$

where:

$\mu$ = one of said fuel gas heat content and percent concentration of gas inerts, $a_o, b_1, c_1, c_2, d_1$ = constants m1, p1, p2 = exponents n = viscosity of the fuel gas, $k_{t1}$ = thermal conductivity of the fuel gas at said first temperature t1, $k_{t2}$ = thermal conductivity of the fuel gas at said second temperature t2, $f_1(k_{t1})$ = first function of fuel gas thermal conductivity at the first temperature, t1, and $f_2(k_{t2}/k_{t1})$ = second function of fuel gas thermal conductivity at the first temperature, t1, and thermal conductivity at the second temperature, t2.

16. The apparatus according to claim 15, wherein the fuel gas comprises natural gas and the first, second and third generated electrical signals are used by said computer signal generating means as a measure of the heat content of the gas and wherein:

$a_o \approx 3643.53$ $b_1 \approx 1050.71$ $d_1 \approx 102$ m1 = 3

$c_1 \approx -7.60221$ p1 = 1

$c_2 \approx -2294.2$ p2 = 1.

17. The apparatus according to claim 15, wherein the fuel gas comprises natural gas and the first, second and third generated electrical signals are used by said computer signal generating means as a measure of the percent concentration of inerts including nitrogen, oxygen and carbon dioxide in the gas and wherein:

$a_o \approx 288.69$ $b_1 \approx -23.818$ $d_1 \approx 102$ m1 = 3

$c_1 \approx -0.59575$ p1 = 1

$c_2 \approx -173.65$ p2 = 1.

18. The apparatus according to claim 15, wherein the fuel gas comprises natural gas and the first, second and third electrical signals are used by said computer signal generating means as a measure of the percent concentration of nitrogen and oxygen in the gas and wherein:

$a_o \approx 464.65$ $b_1 \approx 9.8185$ $d_1 \approx 102$ m1 = 3

$c_1 \approx -0.42180$ p1 = 1

$c_2 \approx -356.18$ p2 = 1.

19. The apparatus according to claim 15, wherein the fuel gas comprises natural gas and the first, second and third electrical signals are used by said computer signal generating means as a measure of the percent concentration of carbon dioxide in the gas and wherein:

$a_o \approx -175.96$
$b_1 \approx -33.636$
$d_1 \approx 102$
$m1 = 3$ $c_1 \approx -0.1739$
$p1 = 1$
$c_2 \approx 182.52$
$p2 = 1.$

* * * * *

UNITED STATES PATENT AND TRADEMARK OFFICE
CERTIFICATE OF CORRECTION

PATENT NO. : 5,311,447
DATED      : May 10, 1994
INVENTOR(S) : Bonne

It is certified that error appears in the above-indentified patent and that said Letters Patent is hereby corrected as shown below:

Column 8, line 65, delete "99333756$_{t1}$" and substitute therefor --9933756$_{t1}$--.

Column 14, line 4, delete "NOMENCLATURE" and substitute therefor --SUBSCRIPTS--.

Column 14, line 4, delete "Symbol" and "Units".

Column 17, line 36, delete "'16509" and substitute therefor -- -16509--.

Column 20, line 67, delete "quality" and substitute therefor --plurality--.

Column 23, line 28, between "$a_o$" and "$b_1$" insert --,--.

UNITED STATES PATENT AND TRADEMARK OFFICE
CERTIFICATE OF CORRECTION

PATENT NO. : 5,311,447
DATED : May 10, 1994
INVENTOR(S) : Bonne

It is certified that error appears in the above-indentified patent and that said Letters Patent is hereby corrected as shown below:

Column 24, line 7, delete "$c_2f_2(k_{t2},k_{t1})P^2$" and substitute therefor --$c_2f_2(k_{t2}/k_{t1})P^2$--.

Signed and Sealed this

Thirteenth Day of September, 1994

Attest:

BRUCE LEHMAN

Attesting Officer

Commissioner of Patents and Trademarks